US010548885B2

(12) United States Patent
Paillard et al.

(10) Patent No.: US 10,548,885 B2
(45) Date of Patent: Feb. 4, 2020

(54) METHOD FOR TREATING MOVEMENT DISORDERS WITH BEFIRADOL

(71) Applicant: PIERRE FABRE MEDICAMENT, Boulogne-Billancourt (FR)

(72) Inventors: Bruno Paillard, Escalquens (FR); Laurence Del Frari, Trebons sur la Grasse (FR); Valérie Brunner, Saint Orens de Garneville (FR); Adrian Newman Tancredi, Castres (FR); Mark Varney, Dana Point, CA (US)

(73) Assignee: PIERRE FABRE MEDICAMENT, Boulogne-Billancourt (FR)

( * ) Notice: Subject to any disclaimer, the term of this patent is extended or adjusted under 35 U.S.C. 154(b) by 0 days.

(21) Appl. No.: 15/310,415

(22) PCT Filed: Jul. 9, 2015

(86) PCT No.: PCT/EP2015/065763
§ 371 (c)(1),
(2) Date: Nov. 10, 2016

(87) PCT Pub. No.: WO2016/005527
PCT Pub. Date: Jan. 14, 2016

(65) Prior Publication Data
US 2017/0239231 A1 Aug. 24, 2017

Related U.S. Application Data

(60) Provisional application No. 62/022,462, filed on Jul. 9, 2014.

(51) Int. Cl.
*A61K 31/4545* (2006.01)
*A61K 9/00* (2006.01)
*A61K 47/38* (2006.01)

(52) U.S. Cl.
CPC ........ *A61K 31/4545* (2013.01); *A61K 9/0053* (2013.01); *A61K 47/38* (2013.01)

(58) Field of Classification Search
CPC .. A61K 31/4545; A61K 9/0053; A61K 47/38; A61K 31/395; A61K 31/495
See application file for complete search history.

(56) References Cited

U.S. PATENT DOCUMENTS

| 5,431,922 A * | 7/1995 | Nicklasson | A61K 9/2027 |
| | | | 424/484 |
| 6,020,345 A | 2/2000 | Vacher et al. | |
| 7,208,603 B2 | 4/2007 | Maurel et al. | |
| 2009/0324710 A1 | 12/2009 | Glidden et al. | |
| 2011/0061345 A1 | 3/2011 | Cherukuri et al. | |

FOREIGN PATENT DOCUMENTS

| CA | 2 813 648 | 4/2013 | | |
| JP | 2011-524416 A | 9/2011 | | |
| RU | 2 390 355 C2 | 5/2010 | | |
| WO | WO 2006/017852 A2 | 2/2006 | | |
| WO | WO 2011/099573 A1 | 8/2011 | | |
| WO | WO 2012/030314 A1 | 3/2012 | | |
| WO | WO 2012/048710 A1 | 4/2012 | | |
| WO | WO 2535048 A1 | 12/2012 | | |
| WO | WO 2013/004249 A1 | 1/2013 | | |
| WO | WO-2013004249 A1 * | 1/2013 | ............. | A61K 45/06 |
| WO | WO 2013/156035 A1 | 10/2013 | | |

OTHER PUBLICATIONS

Viena D. Dias, Kurt Fegely, Abhijit V. Gothoskar and Ali R. Rajabi-Siahboomi, Application of an Aqueous Ethylcellulose Dispersion in Multiple-Unit Pellet Systems, Poster Reprint, Controlled Release Society, Jul. 2007 (Year: 2007).*
Colpaert et al., "Large-amplitude 5-HT$_{1A}$ receptor activation: a new mechanism of profound, central analgesia," Neuropharmacology, vol. 43, 2002, pp. 945-958.
Roppongi et al., "Perospirone in treatment of Huntington's disease: A first case report," Progress in Neuro-Psychopharmacology & Biological Psychiatry, vol. 31, No. 1, 2007 (available online Aug. 1, 2006), pp. 308-310.
Shimizu et al., "Improving the Treatment of Parkinson's Disease: A Novel Approach by Modulating 5-HT$_{1A}$ Receptors," Aging and Disease, vol. 4, No. 1, Feb. 2013, pp. 1-13.
Bruins Slot et al., "Tolerance and Inverse Tolerance to the Hyperalgesic and Analgesic Actions, Respectively, of the Novel Analgesic, F 13640," European Journal of Pharmacology, vol. 466, No. 3, 2003, pp. 271-279 (10 pages total).
Watanabe, Pharmacist Plus, No. 17, 2012, cols. 14-15, with a partial English translation, (6 pages total).
International Search Report issued in PCT/EP2015/065763, dated Sep. 16, 2015.
Written Opinion of the International Searching Authority issued in PCT/EP2015/065763, dated Sep. 16, 2015.
Ministry of Health and Welfare Medical Affairs Bureau Examination Division 1: Biological Product Manager Division Notice of Notification, Guideline on Design and Evaluation of Extended-Release (Oral) Preparations; Notification No. 5, Mar. 11, 1988, pp. 1-9.
Palmer et al., "The Influence of Hydrophilic Pore Formers on Dipyridamole Release from Aqueous Ethylcellulose Film-Coated Pellets", Colorcon, Poster Reprint, AAPS Annual Meeting, Nov. 2007, 5 pages.

* cited by examiner

*Primary Examiner* — Sarah Pihonak
*Assistant Examiner* — Jason Deck
(74) *Attorney, Agent, or Firm* — Birch, Stewart, Kolasch & Birch, LLP

(57) ABSTRACT

The present invention relates to a method of treatment of movement disorders, comprising administering to a patient in need thereof an effective amount of befiradol, where in the administering step provides an average patient's maximum plasma concentration of befiradol below 15 ng/mL which occurs more than 4 hours post administration, said method minimizing side effects of dizziness and nausea. Sustained release pharmaceutical compositions that can be used according to this method are also described.

17 Claims, 1 Drawing Sheet

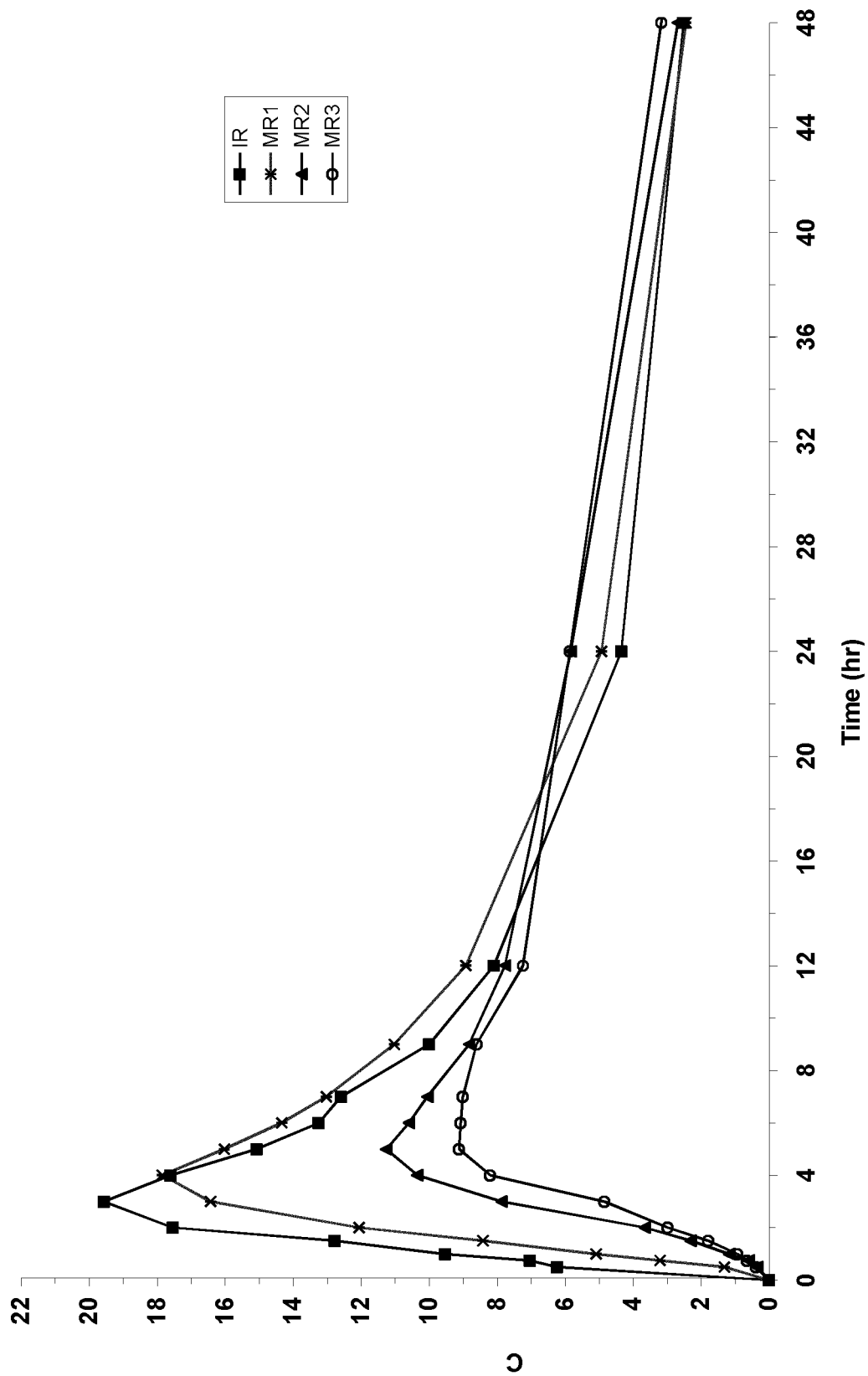

METHOD FOR TREATING MOVEMENT DISORDERS WITH BEFIRADOL

FIELD OF THE INVENTION

The present invention relates to a method of treatment of movement disorders, comprising administering to a patient in need thereof an effective amount of befiradol, wherein the administering step provides an average patient's maximum plasma concentration of befiradol below about 15 ng/mL which occurs more than about 4 hours post administration, said method minimizing side effects of dizziness and nausea. Sustained release pharmaceutical compositions that can be used according to this method are also described.

BACKGROUND OF THE INVENTION

Movement disorders are conditions of the nervous system that affect the intentional ability to produce and control body movement, its speed, fluency, quality, and ease. They usually manifest as abnormal, involuntary movements (dyskinesia) or postures (akinesia) such as chorea (involuntary, rapid, irregular, jerky movements), ballismus (involuntary movements similar to chorea but more violent, explosive), dystonia (involuntary sustained muscle spasms, usually producing twisting, repetitive movements or abnormal postures and positions), myoclonus (twitching or intermittent muscular spasms producing rapid, brief, movements), athetosis (repetitive involuntary, slow, sinuous, writhing movements, especially severe in the hands), akathisia (inability to sit still or remain motionless), ataxia (lack of coordination, often producing jerky movements), syncinesia (the occurrence simultaneously of both voluntary and involuntary movements), tics (involuntary muscle contractions that interrupt normal activities), bradykinesia (slowness or poverty of movement) or tremor (involuntary rhythmic muscle contraction and relaxation involving to and from movements).

Such disorders can occur as a consequence of inherited or acquired diseases, and/or they can result from medical treatments. They are often associated with basal ganglia dysfunction and impaired regulation of dopamine neurotransmission.

For example, Parkinson's disease is caused by degeneration of nerve cells in the substantia nigra and is characterized by pronounced movement impairment, including bradykinesia, rigidity and/or tremor. The quality of life of the patient is progressively decreased, particularly because of disturbed gait and balance. Falls and injuries are a common consequence of balance problems, and represent a threat to the health status and independence of the Parkinson's patient. The symptomatic therapy of Parkinson's disease mainly consists in administering to the patient dopamine-replacing agents that alleviates motor symptoms and greatly improve the quality of life of patients. Levodopa (3,4-hydroxyphenylalanine) which remains the gold standard for treatment of Parkinson's disease, acts as a dopamine prodrug, which is bio-metabolized into dopamine in the brain. Dopamine, in turn, activates dopamine receptors. Direct-acting dopamine receptor agonists such as bromocriptine, lisuride, pramipexole, ropinirole and pergolide are also used mainly in the earlier stages of Parkinson's disease, but are less efficacious than levodopa in moderate to severe Parkinson's disease. However, following long-term dopamine agonist or Levodopa dopamine-replacement therapies, these agents become less efficacious, with the patients switching alternatively from responding periods to non responding periods, and the appearance of side effects such as other involuntary movements, called dyskinesia induced by dopamine-replacement therapy. Parkinson's disease patients may cycle between "on" periods which are complicated by dyskinesia, and "off" periods in which they are severely parkinsonian, and experience profound disability despite the fact that the dopamine replacement remains an effective anti-Parkinson therapy, albeit at narrower and narrower doses, throughout the course of the disease.

Another example of pathology associated with movement disorders is Huntington's disease, a rare, inherited disease that causes chronic progressive chorea and problems with movement coordination. In the early stage of Huntington's disease, slowing of movements, chorea, and occasional loss of balance are significant symptoms. As the disease progresses, balance and walking problems become more serious and incapacitating.

Other examples can be cited such as Tourette's syndrome (an inherited disorder characterized by multiple motor and vocal tics), dystonia (a disorder associated with slowness of movement, poor balance and difficulty moving around) and tardive dyskinesia (a disorder that can result from the use of a number of different pharmacological agents, such as antipsychotic drugs that target the dopamine system, and associated with facial tics and movements of the jaw, lips and tongue).

Many approaches of treatments for movement disorders have been investigated over the past years, few approved therapies having either poor efficacy or tolerability issues. In particular, agonists of the serotonin 5-hydroxytryptamine (5-HT) 1A receptor have been shown to ameliorate and/or prevent some aspects of movement disorders, such as extrapyramidal side effects associated with neuroleptics treatment, dyskinesia that arise from long-term Levodopa therapy in Parkinson's disease (Shimizu et al. 2013 *Aging and disease* 4(1):1-13) or involuntary movement in Huntington's disease (Roppongi et al 2007 *Prog Neuropsychopharmacol Biol Psychiatry* 31(1):308-310).

Befiradol, [(3-Chloro-4-fluoro-phenyl)-[4-fluoro-4-{[(5-methyl-pyridin-2-ylmethyl)-amino]-methyl}piperidin-1-yl] methanone], is a selective and high efficacy serotonin 5-HT1A receptor agonist (Colpaert et al. 2002 *Neuropharmacology* 43: 945-958), discovered by Pierre Fabre Laboratories (U.S. Pat. Nos. 6,020,345; 7,208,603). The structural formula of befiradol is shown below:

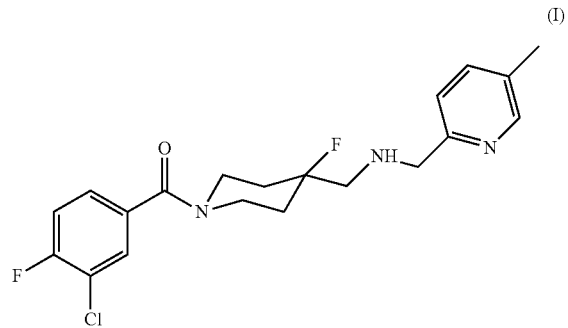 [SMILES: Cc1ccc(CNCC2(F)CCN(C(=O)c3ccc(F)c(Cl)c3)CC2)nc1]

(I)

Befiradol is intended to be of benefit for the treatment of Levodopa-induced dyskinesia and other movement disorders. However, its use to treat patients suffering from movements disorders could be very limited because of its potential side-effects including dizziness and nausea. Indeed, these types of side effects are the most incapacitating in these patient populations because they already experience problems with balance, nausea and emesis, resulting from the movement disorder itself, the underlying pathology and/or the treatment they undergo, such as Levodopa or dopamine agonist administration.

Thus, there is a great need of finding a method to use befiradol to treat movement disorders that would minimize side effects such as dizziness and nausea.

BRIEF SUMMARY OF THE INVENTION

The present invention relates to a method for treating a movement disorder in a patient in need thereof, comprising administering to the patient an effective amount of befiradol or a pharmaceutically acceptable derivative thereof, wherein the administering step provides an average patient's maximum plasma concentration of befiradol below about 15 ng/mL which occurs more than about 4 hours post administration, said method surprisingly minimizing side effects such as nausea and dizziness.

In some embodiments, the effective amount according to the invention is, or is equivalent to, between 0.25 and 3 mg of befiradol base per day of treatment, preferably administered orally.

In some embodiments, the movement disorder according to the invention is induced by the administration of one or several dopamine agonists and/or enhancers, preferably comprising levodopa.

In some preferred embodiments, the movement disorder according to the invention is dyskinesia induced by the administration of one or several dopamine agonists and/or enhancers, preferably comprising levodopa.

In some preferred embodiments, the patient according to the invention is affected by Parkinson's disease.

In some embodiments, at least one sustained release pharmaceutical composition of befiradol or a pharmaceutically acceptable derivative thereof is administered in the method according to the invention, preferably orally.

The invention also relates to a sustained release pharmaceutical composition of befiradol or a pharmaceutically acceptable derivative thereof, comprising a pharmaceutically acceptable excipient that controls the release of befiradol, said composition delivering to a patient an effective amount of befiradol, wherein the average patient's maximum plasma concentration of befiradol is below about 15 ng/mL, and occurs more than about 4 hours post administration.

In some preferred embodiments, the sustained release pharmaceutical composition according to the invention comprises at least one pharmaceutically acceptable excipient that controls the release of befiradol, preferably a polymer, more preferably ethyl cellulose.

In some embodiments, the sustained release pharmaceutical composition according to the invention comprises about 1 to about 20%, preferably about 4 to about 20%, of ethyl cellulose by weight with respect to the total weight of the composition.

In some embodiments, the sustained release pharmaceutical composition according to the invention comprises about 5 to about 20%, preferably about 7 to about 20%, of Surelease E-7-19040™ by dry weight with respect to the total weight of the composition.

BRIEF DESCRIPTION OF THE DRAWINGS

FIG. 1 shows the mean plasma concentrations of befiradol versus time that were observed after a single oral administration of 1 mg of befiradol in four different formulations. Detailed in example 3.

DETAILED DESCRIPTION OF THE INVENTION

A novel method of treatment of movement disorders, comprising administering to a patient an effective amount of befiradol, and surprisingly minimizing side effects of dizziness and nausea, is provided herein.

The inventors found out that controlling the release of befiradol in the patient's plasma, so that the average patient's maximum plasma concentration of befiradol is maintained below about 15 ng/mL and occurs more than about 4 hours post administration, was effective in minimizing side effects of befiradol, such as nausea and dizziness, that would be particularly troublesome to patients with movement disorders. Multiple methods of achieving such a controlled release are provided below.

Definitions

In the context of the present invention, the terms "befiradol" or "befiradol base" refers to [(3-Chloro-4-fluorophenyl)-[4-fluoro-4-{[(5-methyl-pyridin-2-ylmethyl)-amino]-methyl}piperidin-1-yl]methanone].

As used herein, the term "pharmaceutically acceptable" refers to that which is useful in the preparation of a pharmaceutical composition that is generally safe, nontoxic and neither biologically or otherwise undesirable and that is acceptable for veterinary and human pharmaceutical use.

The term "pharmaceutically acceptable derivative" of befiradol includes any isotopic form, salt, solvate, ester, prodrug, or other precursor of befiradol which may be biologically metabolized into befiradol, or crystal form, which are pharmaceutically acceptable, as defined herein, and which have the desired pharmacological activity of befiradol. Pharmaceutically acceptable salts of befiradol include the conventional nontoxic salts of befiradol such as those formed from pharmaceutically acceptable organic or inorganic acids or from pharmaceutically acceptable organic or inorganic bases. As an example, mention may be made of salts derived from inorganic acids such as hydrochloric acid, hydrobromic acid, phosphoric acid and sulfuric acid, and those derived from organic acids such as acetic acid, trifluoroacetic acid, propionic acid, succinic acid, fumaric acid, malic acid, tartaric acid, citric acid, ascorbic acid, maleic acid, glutamic acid, benzoic acid, salicylic acid, toluenesulfonic acid, methanesulfonic acid, stearic acid and lactic acid. As an example, mention may be made of salts derived from inorganic bases such as soda, potash or calcium hydroxide and salts derived from organic bases such as lysine or arginine. These salts may be synthesized from befiradol according to conventional chemical methods well known to the person skilled in the art. In some embodiments, said pharmaceutical acceptable derivative of befiradol is befiradol fumarate.

The terms "treating" or "treatment" are used herein, unless otherwise indicated, to mean to relieve, alleviate, delay, reduce, reverse, improve, or prevent at least one symptom of a disease, disorder or condition. They may also mean to arrest, delay the onset and/or reduce the risk of developing or worsening a disease, disorder or condition.

In the context of the present invention, the term "about" should be understood to mean within an acceptable error range for the particular value as determined by one skilled in the art, which will depend in part on how the value is measured or determined, i.e. the limitations of the measurement system. For example, "about" can mean within 1 or more than 1 standard deviation, per the practice in the art. Alternatively, "about" can mean a range of up to 25%, preferably up to 20%, more preferably up to 10%, more preferably up to 5%, and more preferably still up to 1% of a given value.

In the context of the present invention, the term "dopamine" refers to [4-(2-aminoethyl)benzene-1,2-diol]. The term levodopa refers to [3,4-dihydroxyphenylalanine].

Detailed Description

The present invention concerns a method for treating a movement disorder in a patient in need thereof, comprising administering to the patient an effective amount of befiradol or a pharmaceutically acceptable derivative thereof, wherein the administering step provides an average patient's maximum plasma concentration of befiradol below about 15 ng/mL, which occurs more than about 4 hours post administration, said method minimizing side effects of dizziness and nausea.

The present invention thus also concerns befiradol or a pharmaceutically acceptable derivative thereof for its use in the treatment of a movement disorder in a patient in need thereof, characterized in that it comprises the administration to the patient of an effective amount of befiradol or a pharmaceutically acceptable derivative thereof, providing an average patient's maximum plasma concentration of befiradol or a pharmaceutically acceptable derivative thereof below about 15 ng/mL, which occurs more than about 4 hours post administration, the side effects of dizziness and nausea being minimized.

The present invention also concerns the use of befiradol or a pharmaceutically acceptable derivative thereof for the manufacture of a medicament for the treatment of a movement disorder in a patient in need thereof, characterized in that it comprises the administration to the patient of an effective amount of befiradol or a pharmaceutically acceptable derivative thereof, providing an average patient's maximum plasma concentration of befiradol or a pharmaceutically acceptable derivative thereof below about 15 ng/mL, which occurs more than about 4 hours post administration, the side effects of dizziness and nausea being minimized.

Said administering step is thus designed to produce a specifically low patient's maximum plasma concentration, but also a particular slow rate of increase of plasma concentration of befiradol by delaying the time at which the patient's maximum plasma concentration is attained, so as to minimize side effects of dizziness and nausea. This is notably manifested by a shallow gradient of patient's plasma concentration with respect to time post administration of befiradol, as illustrated, in a non limitative way, by the results of the clinical study detailed in example 3 and FIG. 1.

In some embodiments, said administering step provides an average patient's maximum plasma concentration of befiradol of about 5 ng/mL to about 15 ng/mL.

In some embodiments, said administering step provides an average patient's maximum plasma concentration of befiradol below about 12 ng/mL.

In some embodiments, said administering step provides an average patient's maximum plasma concentration of befiradol of about 5 ng/mL to about 12 ng/mL.

In some embodiments, said patient's maximum plasma concentration of befiradol occurs between about 4 hours and about 12 hours post administration.

In some embodiments, said patient's maximum plasma concentration of befiradol occurs more than about 5 hours post administration.

In some embodiments, said patient's maximum plasma concentration of befiradol occurs between about 5 hours and about 12 hours post administration.

The maximal plasma concentration of befiradol and the time it occurs can be estimated from the concentration of befiradol quantified in plasma samples of the patient after administration.

The quantification of befiradol in plasma samples can be realized with any convenient validated analytical method as determined by those skilled in the art. As example, mention may be made of a validated LC-MS/MS (liquid chromatography-tandem mass spectrometry) bioanalytical method, preferably comprising preparing samples by solid phase extraction using ethyl acetate, drying, dissolving in a mixture of acetonitrile and ammonium acetate, performing a chromatographic separation in this liquid mobile phase and detecting by tandem mass spectrometry. Other bioanalytical methods can be based on techniques such as HPLC (high performance liquid chromatography), GC (gas chromatography), UPLC (ultra performance liquid chromatography), supercritical fluid chromatography, mass spectrometry, nuclear magnetic resonance, electrophoresis, ligand binding assays (dual polarisation interferometry, ELISA—enzyme-linked immunosorbent assay, MIA—magnetic immunoassay, RIA—radioimmunoassay), LC-MS (liquid chromatography-mass spectrometry), GC-MS (gas chromatography-mass spectrometry), LC-DAD (liquid chromatography-diode array detection), CE-MS (capillary electrophoresis-mass spectrometry).

General reference is made to Venn, *Principles and Practice of Bioanalysis* ($2^{nd}$ Edition, CRC Press, 2008)

In some embodiments, said administering step provides a plasma concentration of befiradol over time ($AUC_{inf}$ or total area under the befiradol plasma concentration-time curve) of about 30 hr·ng/mL to about 3000 hr·ng/mL, preferably of about 100 hr·ng/mL to about 1000 hr·ng/mL, preferably of about 300 hr·ng/mL to about 700 hr·ng/mL, more preferably of about 400 to about 500 hr·ng/mL.

In some embodiments, said administering step provides an average patient's maximum plasma concentration of befiradol below about 15 ng/mL (preferably below about 12 ng/mL), which occurs more than about 4 hours (preferably more than about 5 hours) post administration, and a plasma concentration of befiradol over time of about 30 hr·ng/mL to about 3000 hr·ng/mL (preferably of about 100 hr·ng/mL to about 1000 hr·ng/mL, preferably of about 300 hr·ng/mL to about 700 hr·ng/mL, preferably of about 400 to about 500 hr·ng/mL).

Patients

In the context of the invention, the term "patient" refers preferentially to a mammal, more preferentially to a human.

In some embodiments, the patient according to the present invention is affected or very susceptible to being or likely to become affected by a movement disorder.

In some preferred embodiments, the patient according to the present invention is affected by Parkinson's disease.

In some embodiments, the patient according to the present invention experiences one or several of the following disorders: balance disorders, coordination deficits, dizziness, emesis, nausea.

Movement Disorders

As used herein, the term "movement disorder" refers to any condition that affects the movements of a patient, from any origin. For example, movement disorder can refer to a condition of the nervous system that affects the intentional ability to produce and/or control body movements or postures. As examples, mention may be made of dyskinesia, akinesia, bradykinesia, tardive dyskinesia, dopamine replacement therapy induced dyskinesia, levodopa induced dyskinesia, ataxia, akathisia, dystonia, essential tremor, myoclonus, chorea, ballismus, athetosis, tics.

In some embodiments, the movement disorder according to the invention is associated with altered or impaired synaptic dopamine levels.

In some embodiments, the movement disorder according to the invention is associated with a dysfunction of the basal ganglia.

In some preferred embodiments, the movement disorder according to the invention is selected from the group consisting of dyskinesia, chorea, ballismus, dystonia, athetosis, tics, myoclonus.

In some preferred embodiments, the movement disorder according to the invention is dyskinesia.

In the context of the present invention, movement disorders can also refer to a movement disorder associated with diseases such as, for example, Parkinson's disease, Huntington's disease, Tourette's syndrome, Rett syndrome, Wilson's disease, Machado-Joseph disease, restless leg syndrome.

In some preferred embodiments, the movement disorder according to the invention is selected from those associated with Huntington's disease, Tourette's syndrome, or Parkinson's disease.

In some preferred embodiments, the movement disorder according to the invention is associated with Parkinson's disease.

In the context of the present invention, movement disorder can also refer to a movement disorder induced by the administration of one or more drugs, such as, for example, neuroleptics, antipsychotics (e.g. tardive dyskinesia), dopamine agonists and/or dopamine enhancers (e.g. levodopa).

As used herein, the term "dopamine agonist" refers to a substance capable of binding to and activating one ore several dopamine receptors. As an example, mention can be made of bromocriptine, lisuride, pramipexole, ropinirole, pergolide, capergolide, apomorphine, piribedil, talipexole and quinpirole. As used herein, the term "dopamine enhancer" refers to a substance capable of enhancing the release or action of dopamine but which as no specific agonist activity at the dopamine receptors themselves. As an example, mention can be made of dopamine precursors, dopamine prodrugs (e.g. levodopa), drugs that prevent dopamine levels from decreasing, such as inhibitors of mono-amine oxidase (e.g. rasagiline or selegiline), or inhibitors of catechol-O-methyltransferase (e.g. entacapone or tolcapone).

In some embodiments, the movement disorder according to the invention is induced by the administration of one or several dopamine agonists and/or enhancers, preferably comprising levodopa.

In some embodiments, the movement disorder according to the invention is induced by the administration of levodopa.

In some embodiments, the movement disorder according to the invention is tardive dyskinesia induced by neuroleptics and/or antipsychotics, or dyskinesia induced by dopamine agonists and/or enhancers, preferably comprising levodopa.

In some preferred embodiments, the movement disorder according to the invention is dyskinesia induced by the administration of one or several dopamine agonists and/or enhancers, preferably comprising levodopa.

In some preferred embodiments, the movement disorder according to the invention is dyskinesia induced by the administration of one or several dopamine agonists and/or enhancers, preferably comprising levodopa; and the patient according to the invention is affected by Parkinson's disease.

Dosing

As used herein, the term "effective amount" refers to an amount or quantity of a compound which is effective in obtaining the desired therapeutic effect when administered to a patient. It will be appreciated that the precise therapeutic dose will depend on age, condition, weight, etc. of the patient, the route and method of administration, the nature of the condition, disease or disorder being treated and other factors.

As used herein, the expression "equivalent to [ . . . ] of befiradol base" refers, for a derivative of befiradol, to the corresponding amount of befiradol, if it was administered in its base form, as defined herein. As example, 0.65 mg of befiradol fumarate is equivalent to 0.5 mg to befiradol base.

In some embodiments, the effective amount according to the invention is, or is equivalent to, between 0.001 and 1000 mg of befiradol base per day, preferentially between 0.01 and 100 mg of befiradol base per day, preferentially between 0.1 and 10 mg of befiradol base per day, preferentially between 0.25 and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

In some embodiments, the effective amount according to the invention is, or is equivalent to, between 1 and 4 mg of befiradol base per day, preferentially between 1.5 and 3 mg of befiradol base per day, more preferentially between 2 and 2.5 of befiradol base per day, or any one of these particular values, preferentially about 1, 1.5, 2, 2.5, 3, 3.5 or 4 mg of befiradol base per day.

It may be necessary to use doses outside these ranges as determined by the person skilled in the art.

The effective amount according to the present invention may be administered to a patient by various routes, e.g. orally, transdermally, perineurally or parenterally (e.g. by intravenous, subcutaneous, intraperitoneal, or intramuscular injection), among others, including buccal, nasal, ocular, pulmonary, sublingual, and rectal routes. It will be appreciated that the preferred route will depend on the general condition and age of the subject to be treated and the nature of the condition to be treated. In some preferred embodiments, the effective amount according to the invention is administered orally in an appropriate formulation.

In some preferred embodiments, the movement disorder according to the invention is dyskinesia induced by the administration of one or several dopamine agonists and/or enhancers, preferably comprising levodopa; the patient according to the invention is affected by Parkinson's disease; and the effective amount according to the invention is, or is equivalent to, between 0.25 mg and 5 mg of befiradol base per day, preferentially between 0.25 and 3 mg of befiradol base per day, preferentially between 0.5 and 2 mg of befiradol base per day, preferentially between 0.5 to 1.5 mg of befiradol base per day, more preferentially 1 mg of befiradol base per day.

In some preferred embodiments, the movement disorder according to the invention is dyskinesia induced by the administration of one or several dopamine agonists and/or enhancers, preferably comprising levodopa; the patient according to the invention is affected by Parkinson's disease; and the effective amount according to the invention is, or is equivalent to, between 1 and 4 mg of befiradol base per day, preferentially between 1.5 and 3 mg of befiradol base per day, more preferentially between 2 and 2.5 of befiradol base per day, or any one of these particular values, preferentially about 1, 1.5, 2, 2.5, 3, 3.5 or 4 mg of befiradol base per day.

The administration according to the present invention can be realized once a day or several times throughout the day, preferentially once a day or twice a day in equal doses.

Compositions

In some embodiments, the method according to the invention comprises administering to the patient at least one sustained release pharmaceutical composition of befiradol or a pharmaceutically acceptable derivative thereof.

As used herein, the term "pharmaceutical composition" refers to a composition comprising befiradol or a pharmaceutically acceptable derivative thereof and at least one pharmaceutically acceptable excipient.

When used herein, the expression "pharmaceutically acceptable excipient" comprises any substance other than the active compound in a pharmaceutical composition, such as any diluent, additive, adjuvant or excipient. As an example, mention may be made of preservatives, fillers, disintegrators, wetting agents, emulsifiers, dispersants, antibacterial or antifungal agents, solid carriers, flavouring agents, solubilizers, lubricants, glidants, binders, antiadherents, sorbents, encapsulating/coating materials or other agents that would allow a controlled release of the active compound.

In the context of the present invention, the terms "sustained release", "controlled release" or "modified release" refers to compositions that release befiradol (and optionally additional active ingredients) at a time other than promptly after administration, e.g., over an extended period of time that exceeds the duration of befiradol release from conventional immediate release compositions.

The composition according to the invention can comprise any effective amount of befiradol and/or one or more pharmaceutically acceptable derivatives thereof.

In some embodiments, the composition according to the invention comprises between 0.001 and 1000 mg of befiradol and/or one or more pharmaceutically acceptable derivatives, expressed as equivalent amount of befiradol base, preferentially between 0.01 and 100 mg, preferentially between 0.1 and 10 mg, preferentially between 0.25 and 3 mg, preferentially between 0.5 and 2 mg, preferentially between 0.5 to 1.5 mg, more preferentially 0.5 mg, more preferentially 1 mg.

The composition according to the present invention may be administered to a patient by various routes, e.g. orally, transdermally, perineurally or parenterally (e.g. by intravenous, subcutaneous, intraperitoneal, or intramuscular injection), among others, including buccal, nasal, ocular, pulmonary, sublingual, and rectal routes. It will be appreciated that the preferred route will depend on the general condition and age of the subject to be treated and the nature of the condition to be treated. In some preferred embodiments, the composition according to the invention is administered orally in an appropriate formulation.

The composition according to the present invention may take the form of solid, semi-solid, lyophilized powder, or liquid dosage forms, such as, for example, tablets, hard and soft capsules, pills, lozenges, powders, granules, solutions, suspensions, emulsions, syrups, elixirs, suppositories, creams, ointments, lotions, gels, aerosols, patches, implants or the like, preferentially in one or more unit dosage forms suitable for simple administration of precise dosages. In some embodiments, the composition according to the invention takes the form of loaded capsules, preferentially hydroxypropyl cellulose or gelatin capsules.

Methods for preparing such dosage forms are known or will be apparent to those skilled in the art; for example, see Remington, *The science and Practice of Pharmacy* ($21^{th}$ Edition, Mack Publishing Company, 2006).

The composition according to the invention can comprise, depending on the intended mode of administration and the specific formulation, any suitable weight percentage of befiradol and/or one or more pharmaceutically acceptable derivatives thereof, with respect to the total weight of the composition.

In some embodiments, the dosage form according to the invention comprises about 0.001% to about 95% by weight of befiradol and/or one or more pharmaceutically acceptable derivatives thereof, with respect to the total weight of the composition, preferentially about 0.05% to about 50%, preferentially about 0.5% to about 25%, preferentially about 1% to about 10%, preferentially about 1% to about 5%, preferentially about 1% to about 2.5%, with the remainder consisting essentially of pharmaceutically acceptable excipients. Optionally, the composition according to the present invention may further include other medicinal agents.

In some embodiments, the composition according to the invention comprises an inert substrate, diluent or filler. In some embodiments, the composition according to the invention comprises an inert substrate that comprises sugar, more preferably sugar spheres. Other suitable inert substrates, diluents or fillers include, for example, isomalt, dicalcium phosphate dihydrate, calcium sulfate. lactose, mannitol, sorbitol, cellulose, microcrystalline cellulose, cyclodextrin, kaolin, sodium chloride, dry starch, hydrolyzed starches, pregelatinized, starch, silicone dioxide, titanium oxide, magnesium aluminum silicate, or a mixture thereof.

The composition according to the invention can comprise sugar spheres in any suitable size. In some embodiments, the composition comprises sugar spheres having a size of about 100 to about 1000 μm, preferentially about 200 to about 900 μm, preferentially about 300 to about 800 μm. preferentially about 400 to about 600 μm, more preferentially about 500 to about 600 μm.

The composition according to the invention can comprise any suitable amount of the inert substrate or filler (e.g. sugar spheres). In some embodiments, the composition according to the invention comprises about 15% to about 95% by weight of the inert substrate or filler, with respect to the total weight of the composition, preferentially about 50% to about 95%, preferentially about 75% to about 90%. For example, the stable dosage form may comprise about 75% to about 90% by weight of sugar spheres having a size of about 500 to about 600 μm, with respect to the total weight of the composition.

In some embodiments, the composition according to the invention also comprises a binder, preferentially hydroxypropylcellulose. Other suitable binders include, for example, polyvinylpyrrolidone (e.g., Povidone K30), starch, polyvinyl alcohol, pre-gelatinized starch, gelatin, sucrose, glucose, dextrose, lactose, sorbitol, polyethylene glycol, waxes, natural and synthetic gums such as acacia, tragacanth, sodium alginate, hydroxypropylmethylcellulose, ethylcellulose, veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid, or a mixture thereof.

The composition according to the invention can comprise any suitable amount of the binder (e.g., hydroxypropylcellulose). In some embodiments, the composition according to the invention comprises about 0.1% to about 15% by weight of the binder, with respect to the total weight of the composition, preferentially about 1% to about 10%, preferentially about 3% to about 6%.

In some embodiments, the composition according to the invention also comprises an anti-adherent or lubricant, preferentially talc. Other suitable anti-adherents or lubricants include, for example, magnesium stearate, calcium stearate, stearic acid, glycerol behenate, polyethylene glycol, talc, mineral oil, sodium stearyl fumarate or mixtures thereof.

The composition according to the invention can comprise any suitable amount of the lubricant or anti-adherent (e.g. talc). In some embodiments, the composition according to the invention comprises about 0.1% to about 15% by weight of the lubricant or anti-adherent, with respect to the total weight of the composition, preferentially about 0.1% to about 5%, preferentially about 0.1% to about 1%.

According to the invention, the controlled release of befiradol can be achieved by any pharmaceutically acceptable mean as determined by the person skilled in the art.

Systems that can be used to control the release of befiradol according to the invention are known or will be apparent to those skilled in the art; for example, see Remington, *The science and Practice of Pharmacy* (21$^{th}$ Edition, Mack Publishing Company, 2006).

As examples, mention may be made of the following systems:

Diffusion systems: Characterized by the release rate of drug, being dependent on its diffusion through an inert membrane barrier, usually an insoluble polymer.

Dissolution systems: The release of drug is limited by the rate of dissolution of the system. Sustained-release compositions are made by decreasing their rate of dissolution. The approaches to achieve this decrease include preparing appropriate salts or derivatives, coating the drug with a slowly dissolving material, or incorporating it into a tablet with a slowly dissolving carrier.

Osmotic system: Osmotic pressure is used to generate a constant release of drug, using a semi-permeable membrane that is permeable to water, but not to the drug.

Ion-exchange systems: They generally use resins composed of water-insoluble cross-linked polymers. These polymers contain salt-forming functional groups in repeating positions on the polymer chain. The drug is bound to the resin and released by exchanging with appropriately charged ions in contact with the ion-exchange groups. The free drug diffuses out of the resin. The drug-resin complex is prepared either by repeated exposure of the resin to the drug in a chromatography column, or by prolonged contact in solution.

Swelling and expansion systems: Based on hydrogels which swell fast upon contact with water which lead to a large increase in size and a prolonged transit time in the stomach.

Floating systems: If the dosage form has a lower density than the gastric fluids, it will float on a top of the stomach content, allowing for an increased time span to release the drug.

Bioadhesive or mucoadhesive systems: Based on bioadhesive or mucoadhesive polymers such as polyacrylic acid and chitosen to achieve the dosage forms sticking on to the mucosa.

Matrix systems: Consisting in the direct compression of blends of drug, retardant materials and additives to form a tablet in which drug is embedded in matrix core of the retardant.

Methods to produce controlled release systems useful for compositions of the present invention include, but are not limited to, crystallization, condensation, co-crystallization, precipitation, co-precipitation, emulsification, dispersion, high pressure homogenisation, encapsulation, spray drying, coacervation, phase separation, solvent evaporation to produce microspheres, extrusion and supercritical fluid processes.

General reference is made to Wise, *Handbook of Pharmaceutical Controlled Release* (Marcel Dekker Publishing Company, 2000)

In some embodiments, the composition according to the invention comprises at least one pharmaceutically acceptable excipient that controls the release of befiradol. Said excipient can be any controlling agent, polymeric agent or coating agent (e.g. ethyl cellulose). Suitable release controlling agents include, for example, cellulose and cellulose derivative, wax, carbomer, polyalkylene polyol, polycarbophil, methacrylic acid derivative, gelatin, gum, polyethylene oxide, and polyvinyl pyrrolidone, or mixtures thereof.

In some embodiments, said excipient is a polymer, either biodegradable or non-biodegradable; preferentially selected from the group consisting of ethyl cellulose, methyl cellulose, hydroxypropyl cellulose, hydroxyethyl cellulose, hydroxymethyl cellulose, hydroxypropyl methyl cellulose, hydroxypropylmethyl cellulose acetate succinate, hydroxypropylmethyl cellulose phthalate, methylcellulose, cellulose acetate, cellulose acetate phthalate, cellulose acetate trimellitate and carboxymethylcellulose sodium; acrylic acid polymers and copolymers (preferably formed from acrylic acid, methacrylic acid, methyl acrylate, ethyl acrylate, methyl methacrylate and/or ethyl methacrylate), and other methacrylic resins that are commercially available under the trade name Eudragit™ (Evonik), including Eudragit™ L30D-55 and LI00-55, Eudragit™, and Eudragit™ NE, RL and RS; vinyl polymers and copolymers such as polyvinyl pyrrolidone, polyvinyl chloride, vinyl acetate, vinyl acetate phthalate, vinyl acetate crotonic acid copolymer, and ethylene-vinyl acetate copolymer; enzymatically degradable polymers such as azo polymers, pectins, chitosan, amylose, carnauba wax, agar-agar, carob gum, shellac gum, gum Arabic, gum tragacanth, guar gum, alginates, xanthan gum, carregeenan, polysaccharides of mannose and galactose, modified starches, and guar gum; polyethylene; zein and shellac, or mixtures thereof.

In some preferred embodiments, said polymer is ethyl cellulose.

The composition according to the invention can comprise any suitable amount of said excipient that controls the release of befiradol (e.g. ethyl cellulose). In some preferred embodiments, the composition according to the invention comprises about 1% to about 30% by weight of the said excipient with respect to the total weight of the composition, preferentially about 1% to about 25%, preferentially about 1% to about 20%, preferentially about 2% to about 20%, preferentially about 4% to about 20%, preferentially about 4% to about 15%, more preferentially about 8% to about 15%.

In some embodiments, the composition according to the invention also comprises a plasticizer in some preferred embodiments, for example triglycerides, oleic acid, or a mixture thereof.

Other suitable plasticizers include, for example, triethyl citrate, polyethylene glycol, propylene glycol, triacetin, dimethyl phthalate, diethyl phthalate, dibutyl phthalate, dibutyl sebacate, tributyl citrate, triethyl acetyl citrate, glycerolmonostearate, castor oil, acetylated monoglycerides, or a mixture thereof. The composition according to the invention can comprise any suitable amount of the plasticizer (e.g. mixture of oleic acid and triglycerides). In some embodiments, the composition according to the invention comprises about 0.1% to 15% by weight of the plasticizer, with respect to the total weight of the composition, preferentially about 0.1% to about 5%, preferentially about 1% to about 5%.

Aqueous dispersions of ethyl cellulose, also comprising a plasticizer, are commercially available under the trade name Surelease™ (Colorcon). The formula of Surelease E-7-19040™ consists in purified water, ethyl cellulose 20 mPa·s, ammonium hydroxide 28%, triglycerides medium-chain and oleic acid.

In some preferred embodiments, the composition according to the invention comprises an aqueous dispersion of ethyl cellulose, preferentially Surelease E-7-19040™.

The composition according to the invention can comprise any suitable amount of Surelease E-7-19040™. In some preferred embodiments, the composition according to the invention comprises about 1 to about 30% by dry weight of Surelease E-7-19040™, with respect to the total weight of the composition; preferentially about 2% to about 25%, preferentially about 5% to about 20%, preferentially about 7% to about 20%, preferentially about 7% to about 15%, about 9% to about 15%, preferentially about 9.88% or about 14.49%.

In some preferred embodiments, the composition according to the invention comprises about 1% to about 5% by weight of befiradol and/or one or more pharmaceutically acceptable derivatives thereof; about 75% to about 90% by weight of an inert substrate or filler; about 3% to about 6% by weight of a binder; about 2% to about 20% by weight of an excipient that control the release, preferentially about 5% to about 20%, preferentially about 5% to about 15%, preferentially about 9% to about 15%; about 1% to about 5% by weight of a plasticizer; and about 0.1% to about 1% by weight of an antiadherent or lubricant, with respect to the total weight of the composition.

The present invention has also as an object a sustained release pharmaceutical composition of befiradol or a pharmaceutically acceptable derivative thereof, comprising a pharmaceutically acceptable excipient that controls the release of befiradol, said composition delivering to a patient an effective amount of befiradol, wherein the average patient's maximum plasma concentration of befiradol is below about 15 ng/mL, and occurs more than about 4 hours post administration.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The following examples are merely illustrative of the present invention and should not be construed as limiting the scope of the invention in any way.

EXAMPLES

Examples 1 & 2: Sustained Release Oral Compositions of Befiradol Fumarate

| Component | Example 1 Quantity mg/capsule | % [2] | Example 2 Quantity Mg/capsule | % [2] |
|---|---|---|---|---|
| Drug substance | | | | |
| Befiradol fumarate | 0.65 | 1.17 | 0.65 | 1.11 |
| Equivalent to Befiradol | 0.50 | | 0.50 | |
| Excipients | | | | |
| Sugar spheres (500-600 μm) | 47.10 | 84.61 | 47.10 | 80.27 |
| Hydroxypropylcellulose | 2.25 | 4.04 | 2.25 | 3.83 |
| Surelease-clear E-7-19040 ® [1] | 5.50 | 9.88 | 8.5 | 14.49 |
| Talc | 0.17 | 0.31 | 0.18 | 0.31 |
| Total Fill Weight | 55.67 | 100 | 58.68 | 100 |
| Hard capsule [3] | 1 | | 1 | |

[1] Expressed as dry material corresponding to about 25% of aqueous Surelease dispersion.
[2] Expressed by dry weight, of the total weight of the composition.
[3] Hard Capsule shell composition (% w/w): Red iron oxide (0.47%), titanium dioxide (1.0%), yellow iron oxide (0.45%), gelatin (qsp 100%).

Composition of Surelease E-7-19040® (provided by Colorcon): Purified water, ethyl cellulose 20 mPa·s, ammonium hydroxide 28%, triglycerides medium-chain, oleic acid.

Example 3: Pharmacokinetics and Tolerability of Four Compositions of Befiradol Clinical Study Tested Compositions:

1. IR (immediate release) composition: 0.65 mg befiradol fumarate salt (equivalent to 0.50 mg befiradol) and excipients (calcium phosphate dibasic anhydrous, cellulose microcrystalline, silica colloidal anhydrous and magnesium stearate) in sufficient quantitiy for one tablet 2. MR1 (modified release number 1) composition 3. MR2 (modified release number 2) composition (Example 1)

4. MR3 (modified release number 3) composition (Example 2)

| Component | MR1 Composition Quantity mg/capsule | % [2] | MR2 Composition Quantity mg/capsule | % [2] | MR3 Composition Quantity mg/capsule | % [2] |
|---|---|---|---|---|---|---|
| Befiradol fumarate | 0.65 | 1.23 | 0.65 | 1.17 | 0.65 | 1.11 |
| Equivalent to befiradol | 0.50 | | 0.50 | | 0.50 | |

-continued

| Component | MR1 Composition Quantity | | MR2 Composition Quantity | | MR3 Composition Quantity | |
|---|---|---|---|---|---|---|
| | mg/capsule | % [2] | mg/capsule | % [2] | mg/capsule | % [2] |
| Sugar spheres (500-600 µm) | 47.10 | 89.44 | 47.10 | 84.61 | 47.10 | 80.27 |
| Hydroxypropylcellulose | 2.25 | 4.27 | 2.25 | 4.04 | 2.25 | 3.83 |
| Surelease-clear E-7-19040 ® [1] | 2.5 | 4.75 | 5.50 | 9.88 | 8.5 | 14.49 |
| Talc | 0.16 | 0.30 | 0.17 | 0.31 | 0.18 | 0.31 |
| Total Fill Weight | 52.66 | 100 | 55.67 | 100 | 58.68 | 100 |
| Hard capsule [3] | 1 | | 1 | | 1 | |

[1] Expressed as dry material corresponding to about 25% of aqueous Surelease dispersion.
[2] Expressed by dry weight, of the total weight of the composition.
[3] Hard Capsule shell composition (% w/w): Red iron oxide (0.47%), titanium dioxide (1.0%), yellow iron oxide (0.45%), gelatin (qsp 100%).

Methodology:

A phase I, single-centre, study was performed with open label, single dose, incomplete blocks design, testing in a randomized way the 4 compositions of befiradol in 18 healthy male subjects. Subjects were administered in fed conditions with two different formulations of befiradol and were randomly assigned to one of the six following treatment sequences: (IR; MR1), (MR2; IR), (IR; MR3), (MR1; MR2), (MR3; MR1), (MR2; MR3).

The administration was a single, 1 mg (2×0.5 mg capsules or tablets) of befiradol, oral administration in the morning.

The two single dose administrations of each period were separated by 14 days for all the subjects.

Blood samples for pharmacokinetic analyses were performed before morning drug administration (Time 0), then 0.5 h, 0.75 h, 1 h, 1.5 h, 2 h, 3 h, 4 h, 5 h, 6 h, 7 h, 9 h, 12 h, 24 h, 48 h, T72 h, T96 h, T120 h, T144 h after each befiradol administration.

Befiradol was quantified in plasma samples collected during the study using a validated LC-MS/MS (Liquid Chromatography with tadem Mass Spectrometry) bioanalytical method (see details hereafter).

A non compartmental pharmacokinetic analysis was performed using these plasma concentrations with a qualified program (WinNonlin®, version 5.3). Pharmacokinetic parameters were determined for befiradol as follows:

$C_{max}$ (maximum plasma concentration) was estimated directly from the experimental data.

$T_{max}$ (time to reach the maximal plasma concentration) was estimated directly from the experimental data.

$AUC_{last}$ (observed area under the plasma concentration-time curve from zero to the last quantifiable point) was calculated according to linear-up/log-down trapezoidal rule.

$AUC_{inf}$ (total area under the plasma concentration-time curve) was estimated as the sum of two areas, AUClast and AUCext (extrapolated area from the last quantifiable point to infinity; estimated as the ratio Clast/Kel, where Clast is the observed concentration at Tlast and Kel is the terminal phase rate constant).

$T_{1/2}$ (experimental half-life) was calculated as ln2/Kel, with Kel (terminal phase rate constant) estimated using the negative slope of the least square regression analysis of the log-concentration versus time data for the terminal linear position of the curve. Below limit of quantitation values occurring at the last time points were excluded from the analysis.

$F_{rel}$ (relative bioavailability, expressed as %, of each MR formulation versus the IR formulation) was calculated as follows:

$$\frac{\text{GeometricMeanAUCinfMR} * 100}{\text{Geometric Mean AUCinf IR}}$$

The tolerability analysis was descriptive.

LC-MS/MS Bioanalytical Method:

Sample Processing

Plasma samples (500 µL) were prepared by solid phase extraction using 1 mL ChemElut® cartridges (VARIAN). Elution was performed using 2×3 mL of ethyl acetate. The extracts were dried under nitrogen stream. The dry residue was then dissolved in mobile phase and injected into LC/MS-MS system.

Chromatography

The chromatographic separation was performed on a Chromolith Fast Gradient RP 18e, 50×2 mm I.D. column using a mobile phase made of acetonitrile/15 mM ammonium acetate at pH 3 (20/80, v/v). The samples were injected in the Turbo V ESI interface set at 600° C. Detection was achieved by tandem mass spectrometry and a dwell time of 700 ms.

Calibration Range

The response was linear with concentration in the 0.1-100 ng·mL$^{-1}$ range for befiradol. The methodology proved to be specific, accurate and precise. The response versus concentration data was fitted by least-squares linear regression with 1/X$^2$ weighting factor.

Limits of Quantification

The limit of quantification was 0.1 ng·mL$^{-1}$ for befiradol.

Results:

A total of 18 healthy male subjects were included and completed the study. Their mean age was 30.7 years (ranging from 22 to 42 years), mean weight was 78.02 kg and mean height was 180.1 cm.

The mean plasma concentration-time profiles of befidarol (expressed as the geometric mean) that were observed after single oral dose of 1 mg of each formulation in fed conditions in 9 subjects are represented in FIG. 1.

The main pharmacokinetic parameters of befiradol for each formulation are expressed as geometric mean (geometric coefficient of variation %) and [range], except for $T_{max}$, which is expressed as median and [range]. Results are summarized in the table below:

| | $C_{max}$ (ng/mL) | $T_{max}$ (hr) | $AUC_{last}$ (hr*ng/mL) | $AUC_{inf}$ (hr*ng/mL) | $T_{1/2}$ (hr) | $F_{rel}$ (%) |
|---|---|---|---|---|---|---|
| IR | 22.0<br>31%<br>[15.8-34.4] | 2<br>[0.5-4] | 420<br>27%<br>[293-732] | 450<br>27%<br>[313-800] | 39.9<br>16%<br>[29.1-51.6] | — |
| MR1 | 18.2<br>28%<br>[12.3-29.1] | 4<br>[3-5] | 424<br>20%<br>[342-594] | 454<br>22%<br>[358-704] | 41.8<br>25%<br>[27.1-60.7] | 101 |
| MR2 | 11.4<br>37%<br>[7.57-25.8] | 5<br>[4-6] | 393<br>34%<br>[304-881] | 432<br>34%<br>[332-983] | 46.0<br>22%<br>[28.2-58.6] | 96.2 |
| MR3 | 9.9<br>32%<br>[5.68-15.2] | 6<br>[5-9] | 404<br>27%<br>[287-709] | 442<br>30%<br>[307-779] | 39.8<br>21%<br>[30.8-56.1] | 98.3 |

When compared to the IR formulation, all the modifications observed in the pharmacokinetic behaviour of befiradol are related to the increase of the percentage of Surelease-clear E-7-19040® in the coating of the MR formulation. All MR formulations exhibited characteristics of "modified release" formulations resulting in a slowed and prolonged absorption, with delay in $T_{max}$ associated with a decrease of $C_{max}$, without decreasing their relative bioavailability and without increasing their inter-individual variability on pharmacokinetic parameters.

Five (5/18) subjects (2 with the IR formulation and 3 with the MR1 formulation) experienced 7 mild treatment-emergent adverse events.

Each subject reported a 1 to 4-hour episode of mild dizziness, and one of these 5 subjects (IR formulation) also reported a headache and nausea.

These adverse events were consistent with the pharmacological profile of befiradol.

No treatment-emergent adverse events occurred with the MR2 and MR3 formulations.

CONCLUSION

This study showed that administering MR formulations of befiradol coated with respectively 9.88% and 14.49% of Surelease-clear E-7-19040® (MR2 and MR3), providing a mean Cmax less than about 15 ng/mL and a median Tmax greater than about 4 h, succeeded in greatly minimizing side effects of dizziness and nausea as compared to IR and MR1 (coated with 4.75% of Surelease-clear E-7-19040®) formulations of befiradol that provided a mean Cmax greater than about 15 ng/mL, a median Tmax less than about 4 h and so steeper gradients of the patient's plasma concentration of befiradol with respect to time.

REFERENCES CITED

US Patent Documents

U.S. Pat. No. 6,020,345
U.S. Pat. No. 7,208,603

Foreign Patent Documents

Other Publications

Shimizu et al. 2013 *Aging and disease* 4 (1):1-13
Roppongi et al 2007 *Prog Neuropsychopharmacol Biol Psychiatry* 31(1):308-310
Colpaert et al. 2002 *Neuropharmacology* 43: 945-958
Remington, *The science and Practice of Pharmacy* (21$^{th}$ Edition, Mack Publishing Company, 2006)
Wise, *Handbook of Pharmaceutical Controlled Release* (Marcel Dekker Publishing Company, 2000)
Venn, *Principles and Practice of Bioanalysis* (2$^{nd}$ Edition, CRC Press, 2008)

The invention claimed is:

1. A method for treating a movement disorder in a patient in need thereof, comprising administering to the patient an effective amount of befiradol or an ester or salt thereof, wherein the administering step provides an average patient's maximum plasma concentration of befiradol below about 15 ng/mL, which occurs more than about 4 hours post administration, said method minimizing side effects of dizziness and nausea, and
   wherein the effective amount of befiradol or an ester or salt thereof is, or is equivalent to, between 0.25 and 3 mg of befiradol base per day of treatment.

2. The method according to claim 1, wherein said effective amount is administered orally.

3. The method according to claim 1, wherein said movement disorder is induced by the administration of one or several dopamine agonists and/or enhancers.

4. The method according to claim 1, wherein said movement disorder is selected from the group consisting of dyskinesia, chorea, ballismus, dystonia, athetosis, tics and myoclonus.

5. The method according to claim 3, wherein said movement disorder is dyskinesia induced by the administration of one or several dopamine agonists and/or enhancers, comprising levodopa.

6. The method according to claim 1, wherein said movement disorder is selected from those associated with Huntington's disease, Tourette's syndrome, Parkinson's disease, or tardive dyskinesia.

7. The method according to claim 5, wherein said movement disorder is dyskinesia induced by the administration of one or several dopamine agonists and/or enhancers, comprising levodopa, and wherein the patient is affected by Parkinson's disease.

8. The method according to claim 1, wherein at least one sustained release pharmaceutical composition of befiradol or an ester or salt thereof is administered.

9. The method according to claim 8, wherein at least one sustained release pharmaceutical composition of befiradol or an ester or salt thereof is administered orally.

10. The method according to claim 8, wherein said sustained release pharmaceutical composition comprises at least one pharmaceutically acceptable excipient that controls the release of befiradol.

11. The method according to claim 10, wherein said excipient is a polymer.

12. The method according to claim 11, wherein said polymer is ethyl cellulose.

13. The method according to claim 12, wherein said sustained release pharmaceutical composition comprises about 1 to about 20% of ethyl cellulose by weight with respect to the total weight of the composition.

14. The method according to claim 13, wherein said sustained release pharmaceutical composition comprises about 4 to about 20% of ethyl cellulose by weight with respect to the total weight of the composition.

15. The method according to claim 13, wherein said sustained release pharmaceutical composition comprises, by dry weight with respect to the total weight of the composition, about 5 to about 20% of a dispersion consisting of purified water, ethyl cellulose 20 mPa·s, ammonium hydroxide 28%, triglycerides medium-chain and oleic acid.

16. The method according to claim 15, wherein said sustained release pharmaceutical composition comprises, by dry weight with respect to the total weight of the composition, about 7 to about 20% of a dispersion consisting of purified water, ethyl cellulose 20 mPa·s, ammonium hydroxide 28%, triglycerides medium-chain and oleic acid.

17. A method for treating a movement disorder in a patient in need thereof, comprising administering to the patient an effective amount of befiradol or an ester or salt thereof, wherein the administering step provides an average patient's maximum plasma concentration of befiradol of about 5 ng/mL, to about 15 ng/mL, which occurs more than about 4 hours post administration, said method minimizing side effects of dizziness and nausea, and wherein the effective amount of befiradol or an ester or salt thereof is, or is equivalent to, between 0.25 and 3 mg of befiradol base per day of treatment.

* * * * *

UNITED STATES PATENT AND TRADEMARK OFFICE
CERTIFICATE OF CORRECTION

| | | |
|---|---|---|
| PATENT NO. | : 10,548,885 B2 | Page 1 of 1 |
| APPLICATION NO. | : 15/310415 | |
| DATED | : February 4, 2020 | |
| INVENTOR(S) | : Bruno Paillard et al. | |

It is certified that error appears in the above-identified patent and that said Letters Patent is hereby corrected as shown below:

In the Specification

At Column 16, Lines 21 through 24:
Please replace:

" $\dfrac{\text{Geometric Mean AUCinf MR} * 100}{\text{Geometric Mean AUCinf IR}}$ "

With:

$\dfrac{\text{Geometric Mean AUCinfMR} * 100}{\text{Geometric Mean AUCinf IR}}$

--                                                                        --

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*